(12) United States Patent
Meglan et al.

(10) Patent No.: US 11,234,883 B2
(45) Date of Patent: Feb. 1, 2022

(54) OPERATING TABLE FOR ROBOTIC SURGICAL SYSTEMS

(71) Applicant: Covidien LP, Mansfield, MA (US)

(72) Inventors: Dwight Meglan, Westwood, MA (US); Samuel Cordero, Hamden, CT (US)

(73) Assignee: COVIDIEN LP, Mansfield, MA (US)

( * ) Notice: Subject to any disclaimer, the term of this patent is extended or adjusted under 35 U.S.C. 154(b) by 67 days.

(21) Appl. No.: 16/636,151

(22) PCT Filed: Aug. 13, 2018

(86) PCT No.: PCT/US2018/046434
§ 371 (c)(1),
(2) Date: Feb. 3, 2020

(87) PCT Pub. No.: WO2019/036329
PCT Pub. Date: Feb. 21, 2019

(65) Prior Publication Data
US 2020/0368087 A1    Nov. 26, 2020

Related U.S. Application Data

(60) Provisional application No. 62/546,093, filed on Aug. 16, 2017.

(51) Int. Cl.
*A61G 13/08* (2006.01)
*A61G 13/12* (2006.01)

(52) U.S. Cl.
CPC ......... *A61G 13/08* (2013.01); *A61G 13/1265* (2013.01); *A61G 13/1295* (2013.01)

(58) Field of Classification Search
CPC ...... A61G 13/08; A61G 13/10; A61G 13/101; A61G 13/1295
See application file for complete search history.

(56) References Cited

U.S. PATENT DOCUMENTS 3,492,988 A     2/1970   Mare
4,193,149 A     3/1980   Welch
(Continued)

FOREIGN PATENT DOCUMENTS

| CN | 101548833 A | 10/2009 |
|---|---|---|
| DE | 2200823 A1 | 7/1973 |

(Continued)

OTHER PUBLICATIONS

International Search Report dated Dec. 11, 2018, 2019 and Written Opinion completed Dec. 10, 2018 corresponding to counterpart Int'l Patent Application PCT/US2018/046434.

(Continued)

*Primary Examiner* — Fredrick C Conley

(57) ABSTRACT

An actuating system including at least one actuation section that includes a plurality of actuating supports. Each of the actuating supports includes a shaft assembly and configured to be actuated individually. The shaft assembly of each of the plurality of actuating supports is configured to translate between a first position and a second position. In the first position an actuated actuating support is aligned with the remaining of the plurality of actuating supports and in the second position the actuated actuating support is misaligned with the remaining of the plurality of actuating supports.

16 Claims, 10 Drawing Sheets

(56) References Cited

U.S. PATENT DOCUMENTS

| | | |
|---|---|---|
| 4,599,755 A | 7/1986 | Tominaga |
| 4,637,083 A | 1/1987 | Goodwin |
| 4,890,235 A | 12/1989 | Reger et al. |
| 4,914,760 A | 4/1990 | Hargest et al. |
| 4,941,221 A | 7/1990 | Kanzler |
| 5,008,965 A | 4/1991 | Vrzalik |
| 5,029,352 A | 7/1991 | Hargest et al. |
| 5,103,519 A | 4/1992 | Hasty |
| 5,121,512 A | 6/1992 | Kaufmann |
| 5,235,713 A | 8/1993 | Guthrie et al. |
| 5,394,577 A | 3/1995 | James et al. |
| 5,402,542 A | 4/1995 | Viard |
| 5,701,622 A | 12/1997 | Biggie et al. |
| 5,966,763 A | 10/1999 | Thomas et al. |
| 6,049,927 A | 4/2000 | Thomas et al. |
| 6,484,334 B1 | 11/2002 | Borders et al. |
| 7,234,180 B2 | 6/2007 | Horton et al. |
| 7,698,765 B2 | 4/2010 | Bobey et al. |
| 8,828,023 B2 | 9/2014 | Neff et al. |
| 2006/0112489 A1 | 6/2006 | Bobey et al. |
| 2006/0168736 A1 | 8/2006 | Meyer et al. |
| 2007/0101500 A1* | 5/2007 | Fruh .................. A61G 13/02 5/613 |
| 2007/0251011 A1 | 11/2007 | Matta et al. |
| 2008/0000028 A1 | 1/2008 | Lemire et al. |
| 2008/0035156 A1* | 2/2008 | Hyde .................. A61F 5/05 128/845 |
| 2009/0217460 A1 | 9/2009 | Bobey et al. |
| 2010/0218315 A1 | 9/2010 | Hyde et al. |
| 2010/0318239 A1 | 12/2010 | Oexman et al. |
| 2011/0209289 A1 | 9/2011 | Meyer et al. |
| 2014/0137329 A1 | 5/2014 | Beumer |
| 2016/0270994 A1 | 9/2016 | Staudinger et al. |
| 2017/0135890 A1 | 5/2017 | DuBois et al. |

FOREIGN PATENT DOCUMENTS

| | | |
|---|---|---|
| EP | 3292218 A1 | 11/1988 |
| JP | 2013126454 A | 6/2013 |
| WO | 2005058223 A1 | 6/2005 |
| WO | 2010020248 A1 | 2/2010 |
| WO | 2010044843 A1 | 4/2010 |

OTHER PUBLICATIONS

Chinese First Office Action dated May 26, 2021 corresponding to counterpart Patent Application CN 201880052862.5.
Extended European Search Report dated Apr. 6, 2021 corresponding to counterpart Patent Application EP 18845913.5.

\* cited by examiner

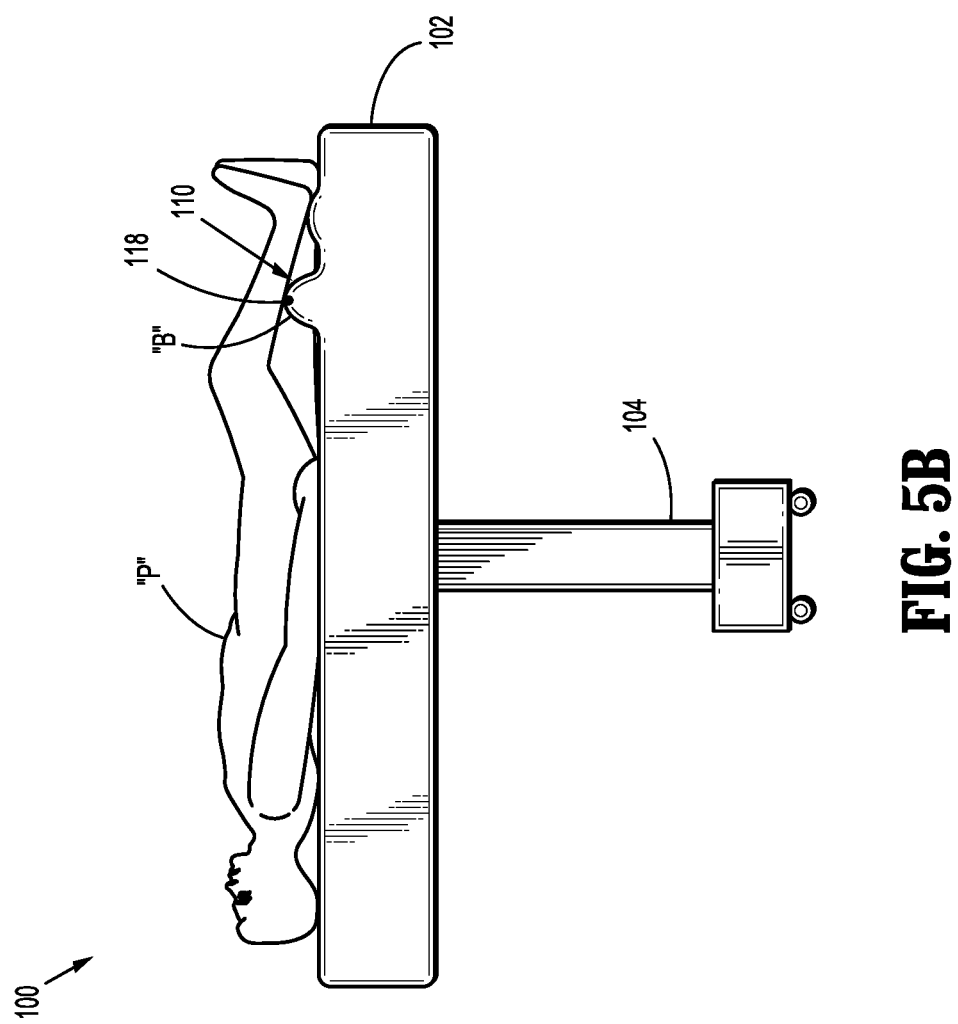

OPERATING TABLE FOR ROBOTIC SURGICAL SYSTEMS

CROSS-REFERENCE TO RELATED APPLICATIONS

This application is a National Stage Application of PCT Application Serial No. PCT/US2018/046434 under 35 USC § 371 (a), filed Aug. 13, 2018, which claims benefit of and priority to U.S. Provisional Patent Application Ser. No. 62/546,093 filed Aug. 16, 2017, the disclosures of each of the above-identified applications are hereby incorporated by reference in their entirety.

BACKGROUND

Traditionally, the mobility of a patient during a medical procedure is limited, if not completely restricted, due to current designs of operating tables. This limitation can cause unnecessary hiccups throughout the medical procedure and potentially limit the range of use for any employed surgical instrument. Additionally, current operating tables prevent the patient from becoming an integral component of the medical procedure. Having an operating table with the capability of constant relative movement of the patient towards the employed surgical device and/or general repositioning would allow the patient to become an integral component of the medical procedure and streamline the entire procedure for the medical staff.

Currently, operating tables can generally be divided into general operating tables and specialty operating tables. Typically, general operating tables provide limited adjustable support to a patient, for example the height and slope of the table may be adjusted by a clinician. This requires manual adjustment of a patient in situations where a targeted area needs to be raised above the general operating table. In these situations, a member of the medical staff will typically position an object, such as a pillow, beneath the targeted area of the patient. However, this is not an ideal method of adjustment.

In comparison, specialty operating tables provide a larger range of adjustments. For example, individual sections of a specialty operating table may be adjusted, that is, entire sections of the specialty operating table are adjustable in relation thereto. Although specialty operating tables provide a larger range of possible adjustments, these tables still lack the ability to constantly move the patient relative to the employed surgical instrument.

Thus, a need still remains for an operating table that provides constant movement of the patient relative to the surgical instrument.

SUMMARY

The present disclosure relates generally to a surgical system. More particularly, the present disclosure relates to a robotic surgical system including an actuating operating table system.

An actuating system including at least one actuating section that includes a plurality of actuating supports. Each of the actuating supports includes a shaft assembly and configured to be activated individually. The shaft assembly of each of the plurality of actuating supports is configured to translate between a first position and a second position. In the first position an activated actuating support is aligned with the remaining of the plurality of actuating supports and in the second position the activated actuating support is misaligned with the remaining of the plurality of actuating supports.

The shaft assembly of each of the plurality of actuating supports includes a head. In the first position the head of the activated actuating support is aligned with the remaining of the plurality of actuating supports and in the second position the head of the activated actuating support is misaligned with the remaining of the plurality of actuating supports. Each shaft assembly also includes an inflatable chamber, wherein the inflatable chamber inflates and deflates moving the shaft assembly between the first position and second position.

Each actuating support of the actuating system includes a base. Each base includes a sensor, a channel configured to receive fluid, and a valve positioned within the channel and electrically coupled to the sensor. The sensor is configured to receive a signal from an operating system which opens and closes the valve to permit ingress and egress of fluid into/from the channel.

The actuating system is configured to simultaneously activate more than one of the plurality of actuating supports. The plurality of actuating supports is configured to reposition a patient relative to a surgical instrument.

In one embodiment, each shaft assembly of the plurality of actuating supports is configured to translate to a third position, wherein the third position is in between the first position and the second position.

In another embodiment, the at least one actuating section is configured to be coupled to an operating table.

A method of positioning a patient during a medical procedure includes determining a desired initial position of the patient upon an actuating operating table system, positioning the patient upon the actuating operating table system, actuating an actuating system of the actuating operating table system to position the patient in the initial position, monitoring the initial position of the patient in relation to a surgical instrument, and actuating the actuating system to maintain the initial position of the patient in relation to the surgical instrument. The desired initial position of the patient is based upon the parameters of the patient.

Actuating the actuating system of the actuating operating table system includes actuating at least one actuating support of the actuating system. The at least one actuating support of the actuating system is transitioned between a first position and a second position.

The method also includes simultaneously moving the surgical device relative to the patient and actuating the actuating system. Additionally, the method further includes monitoring the actuating system.

BRIEF DESCRIPTION OF THE DRAWINGS

The surgical system will be more fully appreciated as the same becomes better understood from the following detailed description when considered in connection with the following drawings, in which:

FIG. 5B is a side view of the actuating operating table of FIG. 5A with at least one activated actuating support.

DETAILED DESCRIPTION

Figure 1:
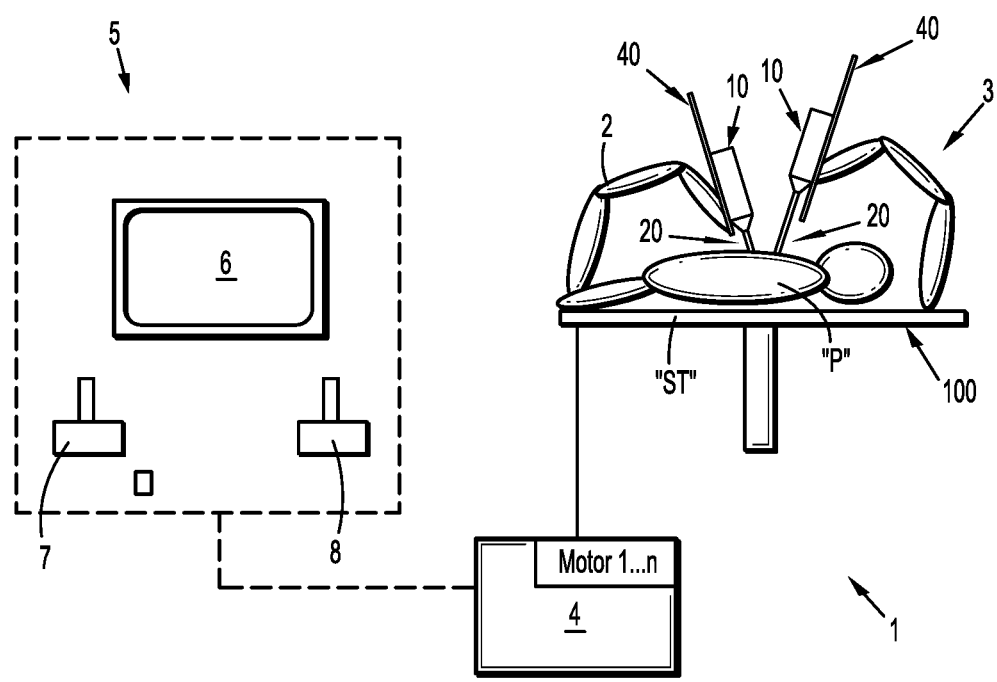
FIG. 1 is a schematic illustration of a robotic surgical system including an actuating operating table in accordance with the present disclosure.

Various embodiments will be described in detail with reference to the drawings, wherein like reference numerals identify similar or identical elements. As commonly known, the term "clinician" refers to a doctor, a nurse, or any other care provider and may include support personnel. Additionally, directional terms such as front, rear, upper, lower, top, bottom, and the like are used simply for convenience of description and are not intended to limit the disclosure attached hereto.

In the following description, well-known functions or constructions are not described in detail to avoid obscuring the present disclosure in unnecessary detail.

In general, the present disclosure relates to a robotic surgical system including an actuating operating table system to facilitate constant movement of a patient's body relative to a surgical instrument during a medical procedure, such that the patient becomes an integral component of the medical procedure. For example, the actuation of the actuating operating table system may manipulate a targeted area relative to a surgical instrument, such that a clinician gains improved access to the targeted area.

Referring initially to FIG. 1, a surgical system, such as, for example, a robotic surgical system 1, generally includes one or more surgical robotic arms 2, 3, a control device 4, an operating console 5, and an actuating operating table system 100. Any of the surgical robotic arms 2, 3 may have a robotic surgical assembly 10 and an electromechanical surgical instrument 20 coupled thereto. In some embodiments, the robotic surgical assembly 10 may be removably attached to a slide rail 40 of one of the surgical robotic arms 2, 3. In certain embodiments, the robotic surgical assembly system 100 may be fixedly attached to the slide rail 40 of one of the surgical robotic arms 2, 3.

The operating console 5 includes a display device 6, which is set up to display three-dimensional images; and manual input devices 7, 8, by means of which the clinician (not shown), is able to telemanipulate the robotic arms 2, 3 in a first operating mode, as known in principle to a person skilled in the art. Each of the robotic arms 2, 3 may be composed of any number of members, which may be connected through joints. The robotic arms 2, 3 may be driven by electric drives (not shown) that are connected to the control device 4. The control device 4 (e.g., a computer) is set up to activate the drives, for example, by means of a computer program, in such a way that the robotic arms 2, 3, the attached robotic surgical assembly 10, and thus the electromechanical surgical instrument 20 (including the electromechanical end effector, not shown) execute a desired movement according to a movement defined by means of the manual input device 7, 8. The control device 4 may also be set up in such a way that it regulates the movement of the robotic arms 2, 3 and/or of the drives.

The robotic surgical system 1 is configured for use on a patient 'P'' positioned (e.g., lying) on the actuating operating table system 100 to be treated in a minimally invasive manner by means of a surgical instrument, e.g., the electromechanical surgical instruments 20. The robotic surgical system 1 may also include more than two robotic arms 2, 3, the additional robotic arms likewise connected to the control device 4 and telemanipulatable by means of the operating console 5. A surgical instrument, for example, the electromechanical surgical instrument 20 (including the electromechanical end effector thereof), may also be attached to any additional robotic arm(s).

For a detailed discussion of the construction and operation of a robotic surgical system, reference may be made to U.S. Pat. No. 8,828,023, filed on Nov. 3, 2011, entitled "Medical Workstation," the entire content of which is incorporated by reference herein.

Turning now to FIGS. 2A, 2B, 3, 3A, 4, 4A, and 4B an embodiment of an actuating operating table system 100 includes an operating system 160, an actuating system 110, and an operating table 102.

The operating system 160 of the actuating operating table system 100 provides a clinician with the ability to control the actuating system 110 of the actuating operating table system 100. The operating system 160 is a real-time operating system that permits the clinician to actuate the actuating system 110 of the actuating operating table system 100 throughout the entire medical procedure. Additionally, the operating system 160 provides visual representation of the actuating system 110 before, during, and after the medical procedure. The operating system 160 may be incorporated in the operating console 5 of the surgical system 1 or may be an individual unit. In embodiments where the operating system 160 is an individual unit, the operating system 160 may be a mobile hand-held device. The operating system 160 may include a memory 162, an application 164, a processor 166, a display 168, a network interface 170, an input device 172, and/or an output module 174.

The memory 162 includes any non-transitory computer-readable storage media for storing data and/or software that is executable by the processor 166 and which controls the operation of the operating system 160. In an embodiment, the memory 162 may include one or more solid-state storage devices such as flash memory chips. The memory 162 may store the application 164.

The application 164 provides the clinician the ability to actuate the actuating system 110 of the actuating operating table system 100. The application 164 may be one or more software programs stored in the memory 162 and executable by the processor 166 of the operating system 160. The application 164 is configured to send and receive information from the actuating system 110 of the actuating operating table system 100. Also, the application 164 may, when executed by the processor 166, cause the display 168 to present user interfaces, such as the user interface 180 illustrated in FIG. 3A.

The processor 166 may be a general purpose processor, a specialized graphics processing unit (GPU) configured to perform specific graphics processing tasks while freeing up the general processor to perform other tasks, and/or number or combinations of such processors.

The display 168 may be touch sensitive, voice activated, and/or motion activated, enabling the display 168 to serve as both an input and output device. The display 168 visually displays different parameters of the actuating system 110, which will be discussed in further detail below.

The network interface 170 may be configured to connect to a network such as a local area network (LAN) consisting of a wired network and/or a wireless network, a wide area network (WAN), a wireless mobile network, a Bluetooth network, and/or the internet. The operating system 160 may receive updates to its software, for example, the application 164, via the network interface 170.

The input device 172 may be any device by means of which the clinician may interact with the operating system 160, such as, for example, a mouse, keyboard, foot pedal, touch screen, and/or voice interface.

The output module 174 may include any connectivity port or bus, such as, for example, parallel ports, serial ports, universal serial busses (USB), or any other similar connectivity port known to those skilled in the art.

With continued reference to FIGS. 2A, 4, 4A and 4B, the actuating system 110 includes actuating sections 112, and actuating supports 120. The actuating system 110 may include a first actuating section 112A, a second actuating section 112B, and a third actuating section 112C, for example. The first section 112A may be positioned proximate to the top or head of the operating table 102, while the third section 112C may be positioned proximate to the bottom or foot of the operating table 102. The second section 112B may be positioned between the first and second sections 112A, 112B. Each of the actuating section 112 of the actuating system 110 may take any appropriate shape or profile, for example, rectangular, circular, or freeform. Additionally, each of the actuating section 112 of the actuating system 110 may have similar dimensions to one another. The length of each of the actuating section 112 may range from 6 inches to 12 inches, and the width of each of the actuating section 112 may range from 2 inches to 6 inches. Each of the actuating sections 112 includes an upper layer 114. The upper layer 114 is configured to translate at least between a neutral position "A" (FIG. 5A) and to a raised positioned "B" (FIG. 5B) in reaction to the actuating supports 120.

Figure 3:
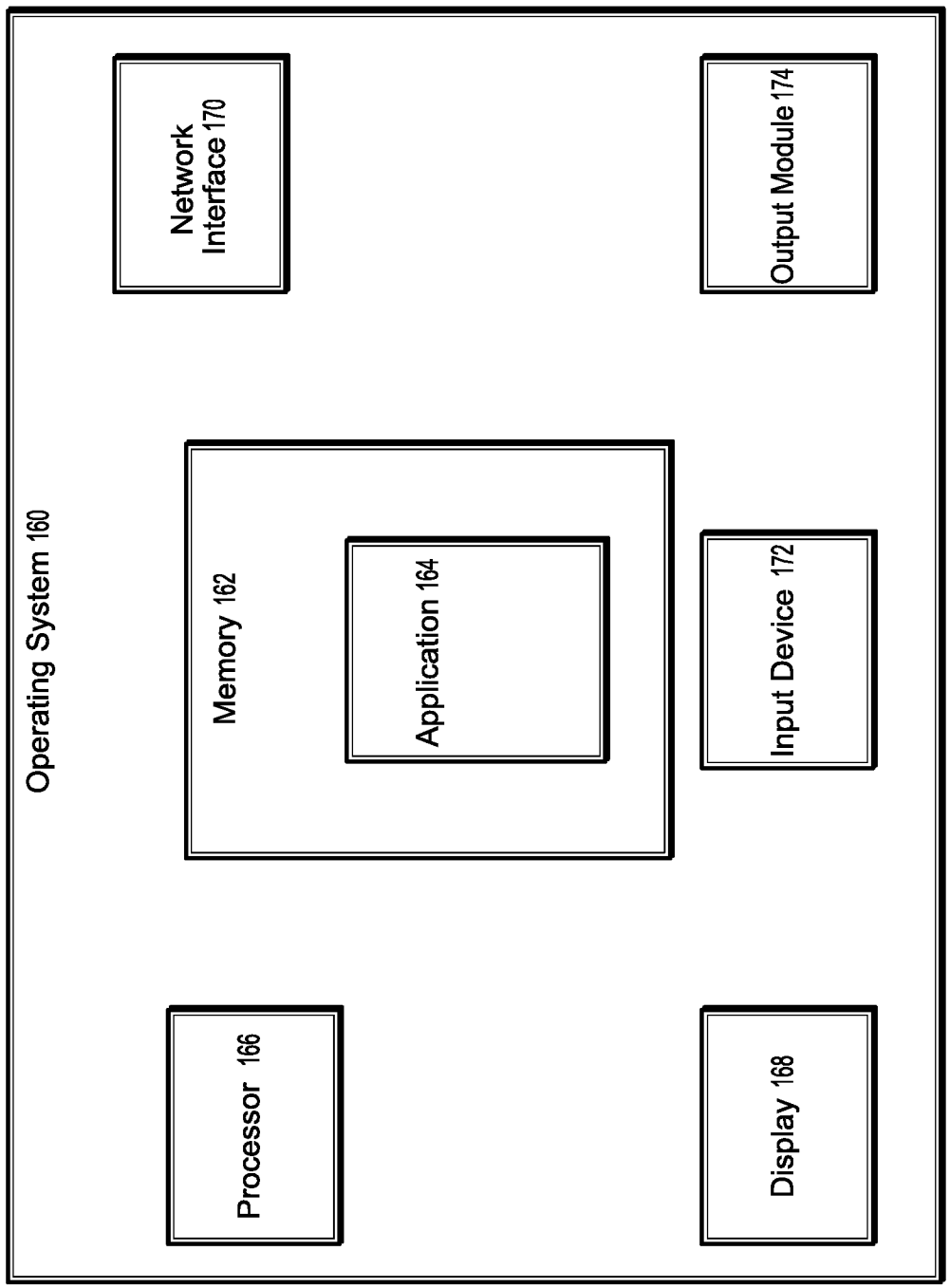
FIG. 3 is a schematic diagram of an operating system which forms part of the robotic surgical system of FIG. 1 in accordance with the present disclosure.
Figure 3A:
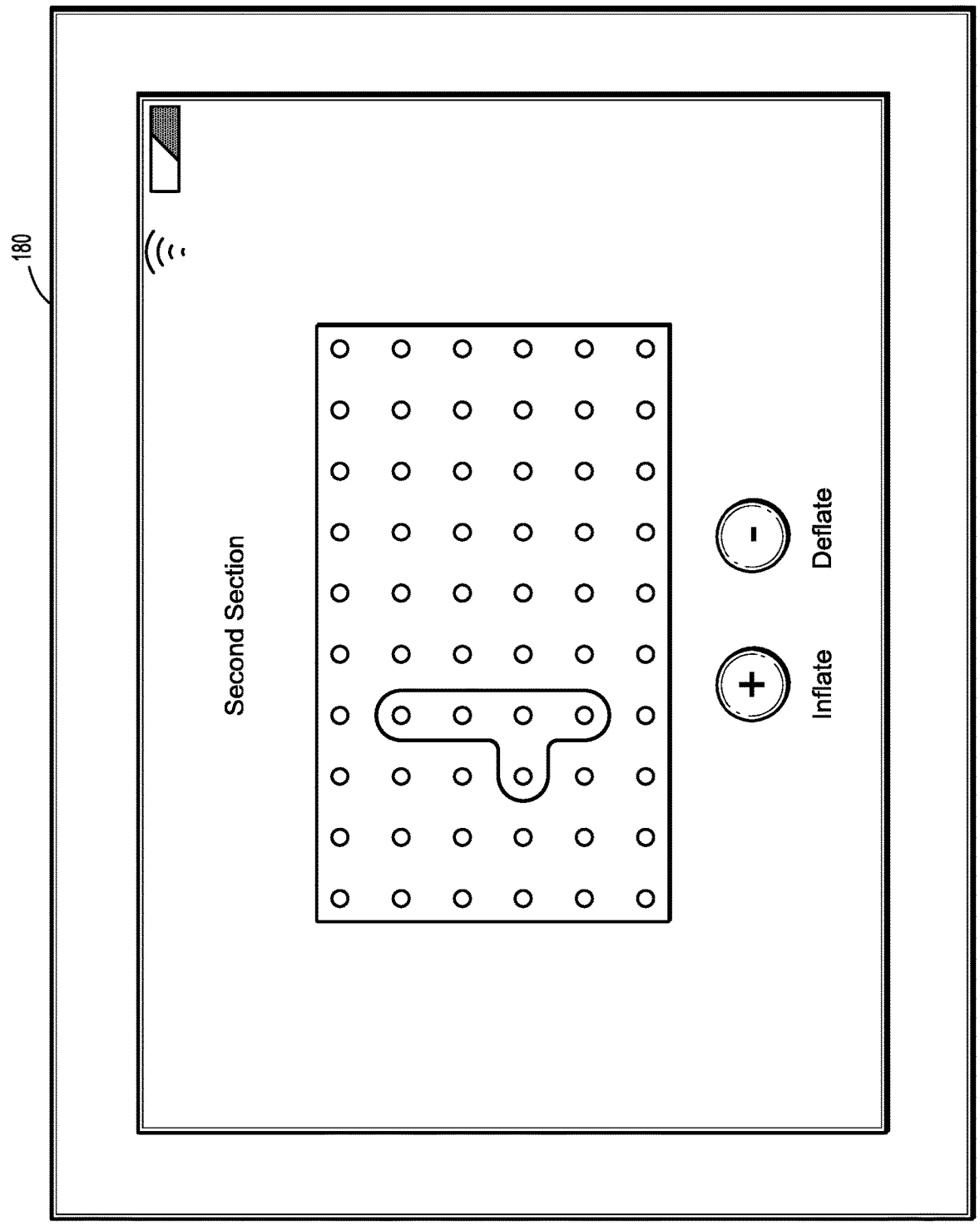
FIG. 3A is an illustration of a user interface presenting a view showing a section of the actuating operating table in accordance with the present disclosure.

The clinician may select the dimensions of each actuating section 112 of the actuating system 110 and/or the number of actuating sections 112 based on the parameters of the patient and the medical procedure. In some embodiments, the actuating system 110 may include fewer actuating sections 112, for example a single actuating section (not illustrated), and/or the actuating system 110 may include more actuating sections 112, for example, more than three actuating sections (not illustrated). The clinician may considered a number of different patient parameters, for example the height and the weight of the patient. The patient's parameters and the parameters of the medical procedure may be uploaded and stored within the operating system 160 and displayed via user interface 180 (FIG. 3A). The clinician can access the patient's parameters and the parameters of the medical procedure throughout the entire duration of the medical procedure.

In some embodiments, each actuating section 112 of the actuating system 110 may be integrally formed with the operating table 102. In other embodiments, each actuating section 112 of the actuating system 110 may be individually movable and attachable to a top surface of the operating table 102.

Figure 2A:
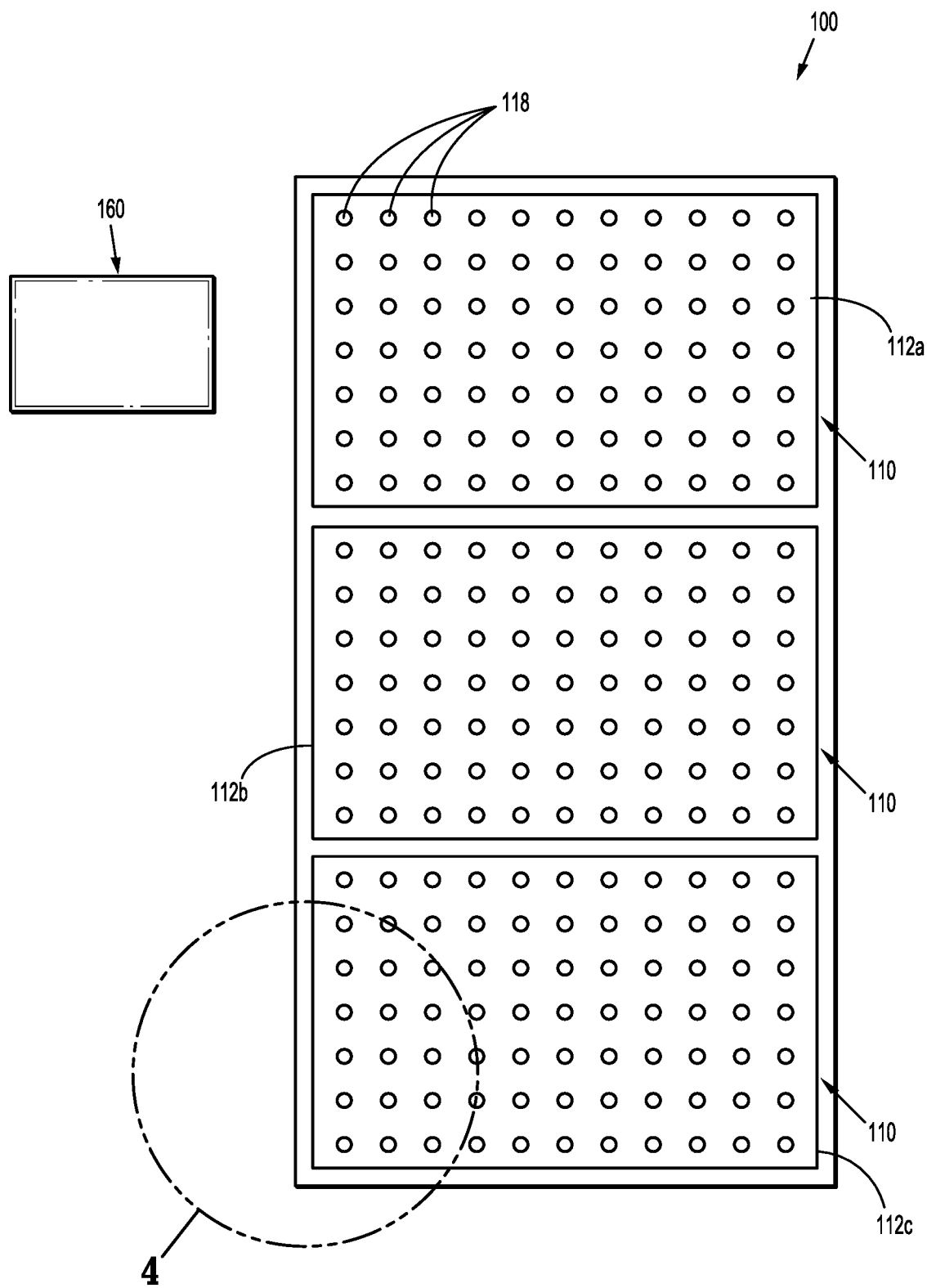
FIG. 2A is a top view of the actuating operating table of FIG. 1.

Each actuating section 112 supports actuation points or plugs 118, as seen in FIG. 2A. The actuation points 118 are positioned upon the upper surface 114 of each actuating section 112 of the actuating system 110. The number of the actuation points 118 of each actuating section 112 and the layout of the actuation points 118 of each actuating section 112 may be selected based on the clinician's needs. The number and layout of the actuation points 118 correspond to the number of actuating supports 120, as described below. Each actuation point 118 may take any appropriate form, for example, a circle, an oval, and/or a square.

Figure 4:
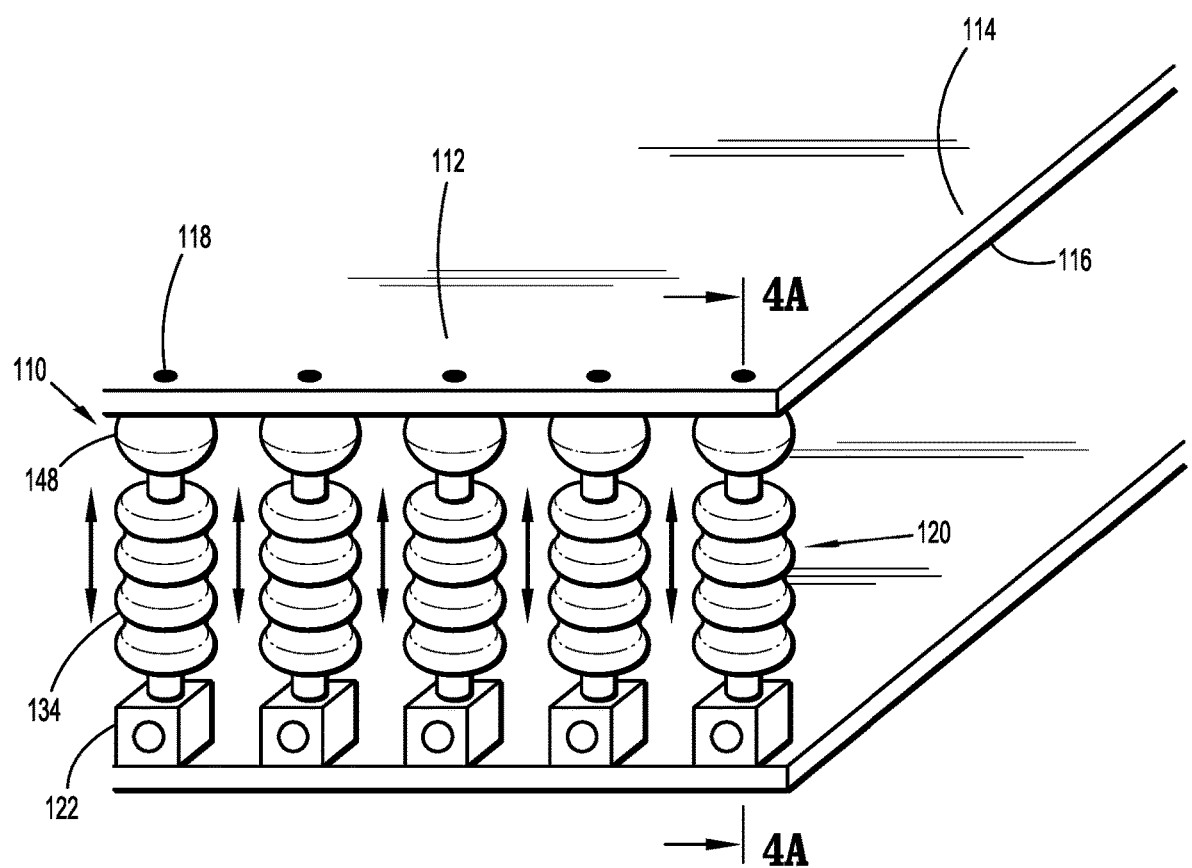
FIG. 4 is an perspective view of an actuating system of the actuating operating table of FIG. 2A.
Figure 4A:
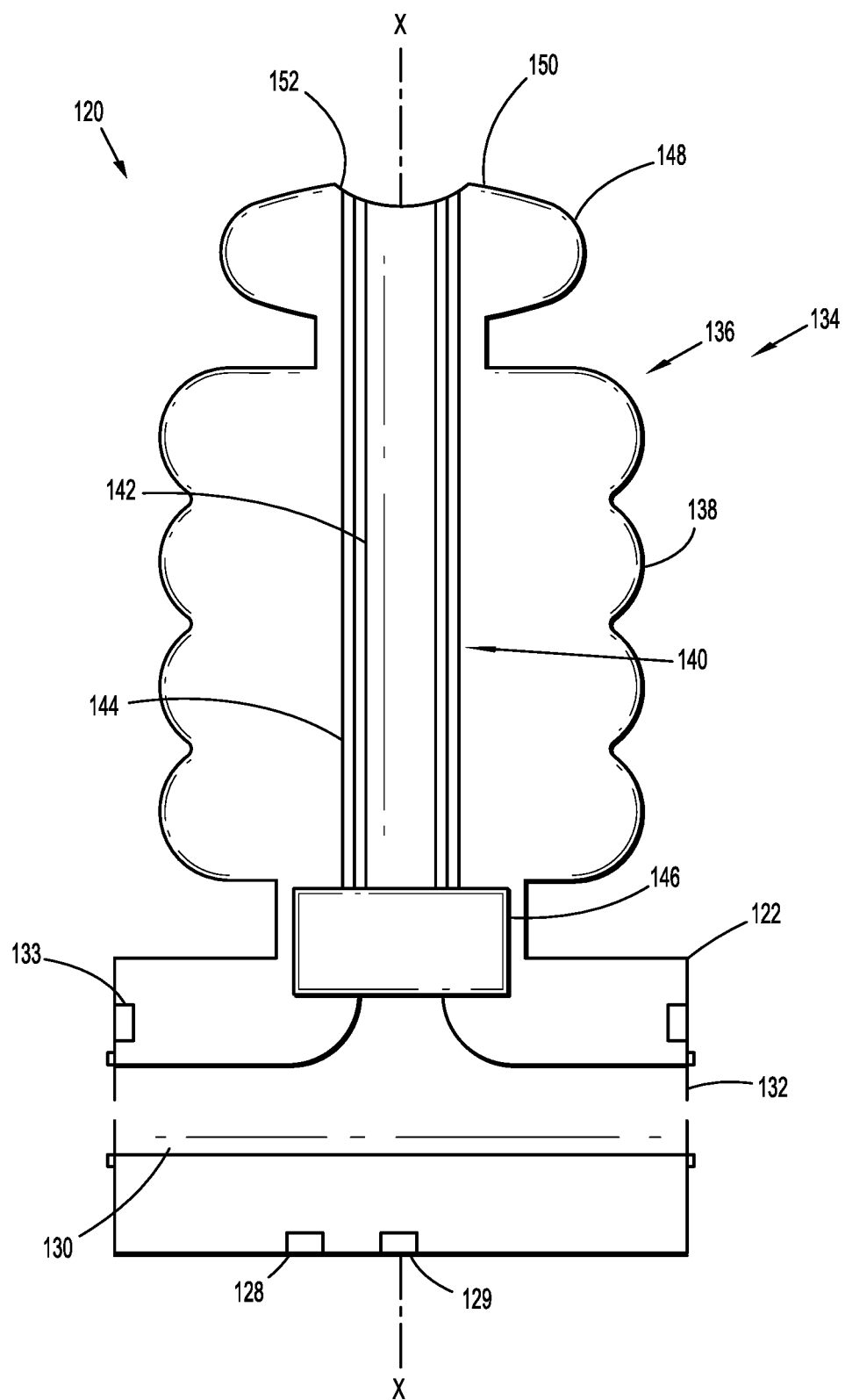
FIG. 4A is a cross-section of an actuating support of the actuating system of FIG. 4 as taken along section line 4A-4A in FIG. 4.
Figure 4B:
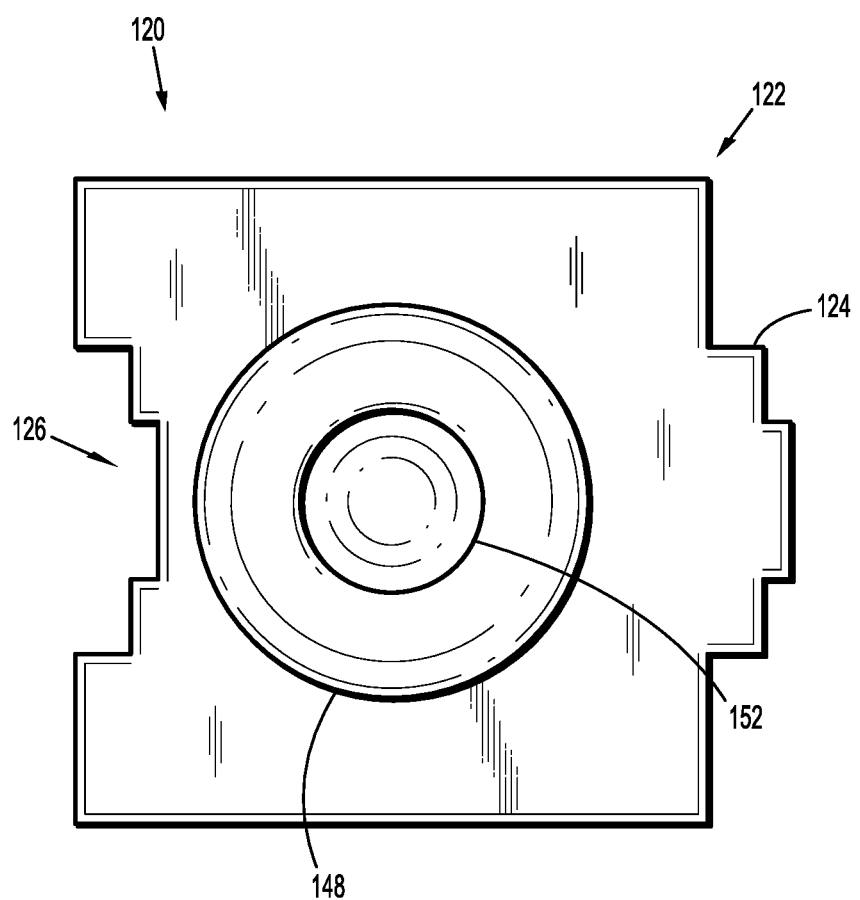
FIG. 4B is a top view of an actuating support of the actuating system of FIG. 4.

Specifically referring to FIGS. 4, 4A, and 4B, the actuating supports 120 each include a base 122 and a shaft assembly 134.

Each base 122 includes a connecting protrusion 124 (FIG. 4B), a receiving groove 126 (FIG. 4B), a transceiver 128 (FIG. 4A) housed within the base 122, a sensor 129 (FIG. 4A), a channel 130 defined therethrough, a valve 132 (FIG. 4A), a valve sensor 133 (FIG. 4A). Each base 122 is configured to connect with one another via the receiving groove 126 and the connecting protrusion 124. The receiving groove 126 is configured and adapted to receive the connecting protrusion 124. In one embodiment, the connecting protrusion 124 may be positioned within the receiving groove 126 by vertically aligning the connecting protrusion 124 of one of the base 122 with the receiving groove 126 of another one of the base 122 and vertically translating the connecting protrusion 124 of one of the base 122 in relations to the receiving groove 126 of the other base 122 (e.g., in the manner of a dovetail connection).

The transceiver 128 housed within each base 122 is capable of receiving a signal from the operating system 160, and transmitting that signal to the valve sensor 133. The signal received by the transceiver 128 and sent to valve sensor 133, will actuate the valve sensor 133 thereby actuating support 120. The transceiver 128 may be any transceiver configured to receive a signal from the operating system 160 and transmit that signal to the valve sensor 133.

The channel 130 is defined through each base 122 transverse to a vertical axis "X" of shaft assembly 134. The channel 130 is configured to receive a fluid, such as air, via a pneumatic pump (not illustrated) that may be connected to the base 122. The channel 130 is positioned relative to the inflatable chamber 146 of the shaft assembly 134, such that upon receiving a signal from the operating system 160, the fluid passing through the channel 130 will enter into the inflatable chamber 146 of the shaft assembly 134. The fluid passing through the channel 130 may enter within the inflatable chamber 146 of the shaft assembly 134 via the valve 132. The valve 132 is electrically coupled to the transceiver 128 via valve sensor 133. When the surgeon selects which actuating support 120 to actuate/activate, the operating system 160 will send a signal to the transceiver 128 of the selected actuating support 120 which in turn will send the signal to the valve sensor 133 opening and/or closing the valve 132 to allow the desired amount of fluid to enter within the inflatable chamber 146 of the shaft assembly 134, thus actuating the selected actuating support 120.

The sensor 129 housed within each base 122 is capable of measuring the height of the shaft assembly 134. In one embodiment, sensor 129 is an ultrasound sensor capable of receiving reflected light or reflected laser (not illustrated). Sensor 129 continually measures the height of the shaft assembly 134. Sensor 129 may be any sensor capable of measuring the fluctuating height of shaft assembly 134. Sensor 129 is configured to transmit the fluctuating height measurement of shaft assembly 134 to the operating system 160.

Each base 122 is securable to the operating table 102 of the actuating operating table system 100. In some embodiments, each base 122 is integrally formed with the operating table 102 of the actuating operating table system 100. In other embodiments, the base 122 is releasably secured to the operating table 102, such that each base 122 may be rearranged or removed from the operating table 102. Each shaft assembly 134 includes a shaft 136 including compression rings 138 forming a sleeve or bellows, an inflatable chamber 146, a rigid member 140, and a head 148. The compression rings 138 may be integrally formed with the shaft 136. The compression rings 138 of the shaft 136 are spaced apart from one another, which allow each compression ring 138 to be compressed in relation to the other compression rings 138 of the shaft 136.

The inflatable chamber 146 may be positioned at the bottom of each shaft assembly 134. The inflatable chamber 146 is configured to receive fluid from the pneumatic pump (not illustrated) via the channel 130 and the valve 132 of the base 122. Depending on amount of fluid received by the inflatable chamber 146 will either inflate or deflate.

The rigid member 140 includes a first cylinder member 142 and a second cylinder member 144. The second cylinder member 144 is configured and dimensioned to fit within the first cylinder member 142, such that an outer diameter of the second cylinder member 144 is comparable to an inner diameter of the first cylinder member 142. The rigid member 140 is positioned on top of the inflatable chamber 146 so that the second cylinder member 144 transitions between a first position and a second position in response to the inflation and deflation of the inflatable chamber 146. The rigid member 140 provides limited support to the shaft assembly 134; rather the rigid member 140 provides guidance for the expansion of the shaft assembly 134.

The head 148 of each shaft assembly 134 extends from the shaft 136 and may be integrally formed therewith. Each head 148 may be positioned adjacent to a lower surface 116 of each actuating section 112 of the actuating system 110. Each head 148 of the shaft assembly 134 may include at least a partially flat surface 150. The partially flat surface 150 may define a dent 152, which may be centrally defined therein. The dent 152 may be configured and dimensioned to receive a respective actuation point 118 therein. In this manner, each actuating support 120 will be centrally aligned with a corresponding actuation point 118. Additionally, the actuation point 118 secures the actuating sections 112 to the heads 148 of the shaft assemblies 134, for example, by a threaded connection or the like.

Figure 5A:
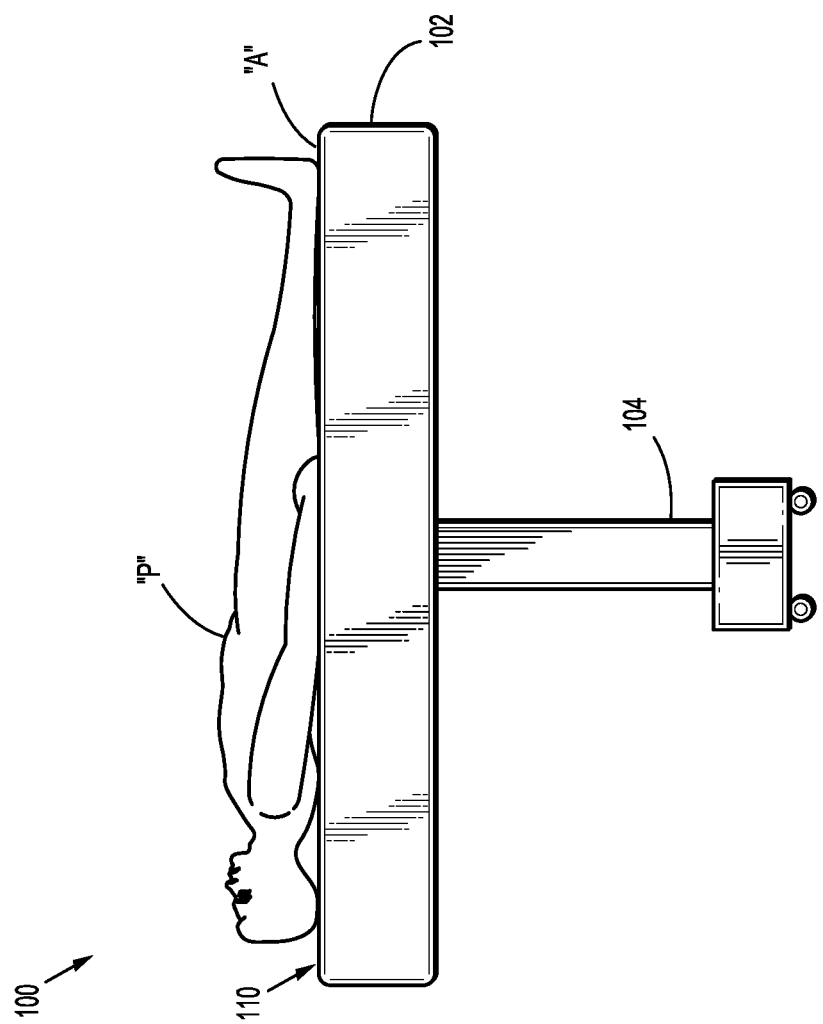
FIG. 5A is a side view of an actuating operating table with inactivated actuating supports in accordance with the present disclosure.

Each shaft assembly 134 is configured to translate between at least a first position and a second position. In the first position, the compression rings 138, the rigid member 140, and the inflatable chamber 146 of the shaft assembly 134 are fully compressed/deflated and the actuation point 118 is positioned in a neutral position. Also in the first position, the head 148 of the shaft assembly 134 remains in contact with the lower surface 116 of the actuating section 112, with the upper surface 114 of the actuating section 112 remaining in a neutral position "A" (FIG. 5A). As each shaft assembly 134 transitions between the first and the second positions, the compression rings 138, the rigid member 138, and the inflatable chamber 146 of the shaft assembly 134 become decompressed/deflated and/or extended/inflated. This decompression and/or extension in turn translates each actuation point 118 between the neutral position and a raised position. In the second position, the compression rings 138, the rigid member 140, and the inflatable chamber 146 will be fully decompressed/inflated and actuation point 118 positioned in a fully raised position. Also, the head 142 of the shaft assembly 134 remains in contact with the lower surface 116 of the actuating section 112. In this manner, the head 148 of the shaft assembly 134 raises the upper surface 114 of the actuating section 112, including the actuation point 118, to a raised positioned "B" (FIG. 4B).

Figure 2B:
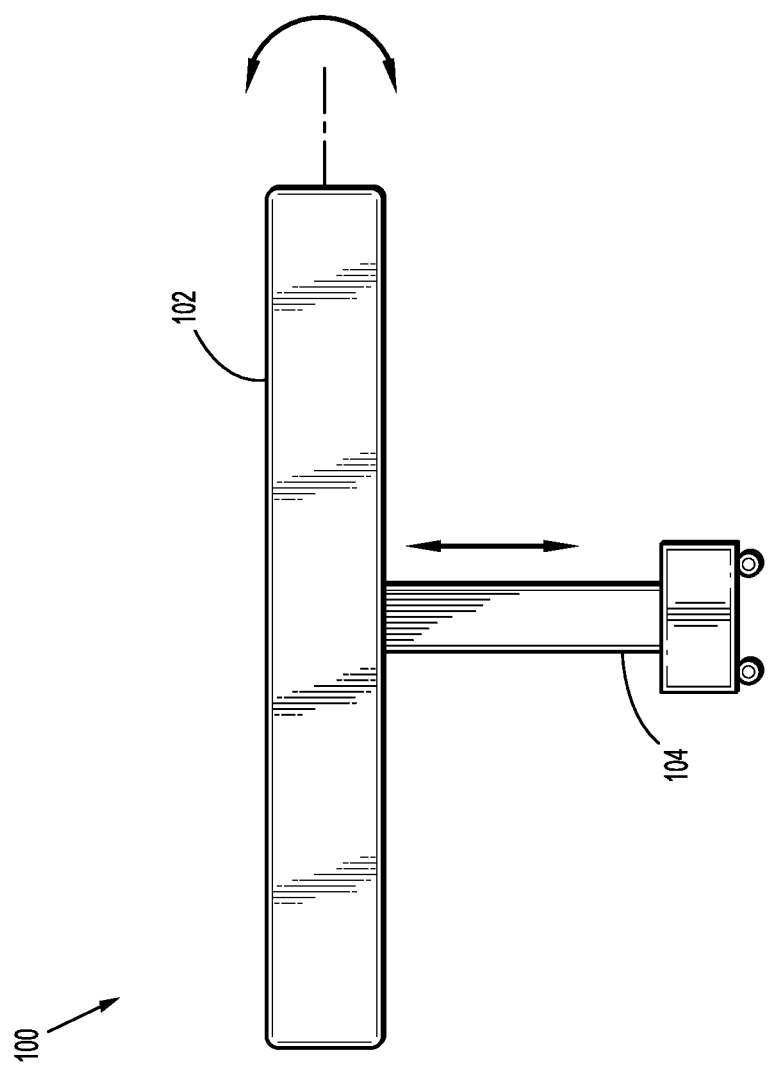
FIG. 2B is a side view of the actuating operating table of FIG. 1.

Each actuating support 120 of the actuating system 110 may be individually actuated, such that the clinician may individual select which the actuating support 120 to actuate via the operating system 160. The operating table 102 is mounted to a base 104 (FIG. 2B). The base 104 of the operating table 102 is configured to adjust the height and slope of the operating table 102.

Each actuating section 112 may be formed of any suitable biocompatible material. For example, the actuating support 120 may be stainless steel, cobalt alloys, and titanium alloys. The upper surface 114 of each actuating section 112 may be flexible biocompatible material.

Moving to FIGS. 5A and 5B, an embodiment of the actuating operating table system 100, shown in use, is illustrated. Initially, the patient's parameters will be gathered and entered into the operating system 160. With this information, the operating system 160 will calculate and provide instruction for an optimal placement, or a suggested placement, of the actuating operating table system 100 in relation to the remaining components of the robotic surgical system 1. Further, the operating system 160 will indicate an optimal or suggested initial position of the patient upon the actuating operating table system 100. Prior to positioning the patient upon the actuating operating table system 100, each actuating support 120 may be unactuated and positioned in the first positioned, e.g., position "A" (FIG. 5A). The clinician may reference the operating system 160 when positioning the patient upon the actuating operating table system 100 to ensure optimal initial positioning. The operating system 160 may provide a signal to the clinician when the patient is optimally positioned upon the actuating operating table system 100. The operating system 160 may also identify parameters of each actuating support 120 and/or the actuating system 110 as a whole throughout the entire procedure. The parameters displayed on the user interface 180 of the operating system 160 may include the percentage of inflation of each actuated/activate actuating support 120, which of the actuating support 120 is actuated, the height of each actuated actuating support 120, or any other parameter of the actuating system 110.

After the patient is positioned upon the actuating operating table system 100, the clinician may actuate any of the actuating supports 120 (FIG. 5B). The clinician may select which the actuating support 120 to actuate based upon the patient's parameter, the specific medical procedure being performed, the surgical instrument being used and/or any combination thereof. The clinician can continually actuate each actuating support 120, translating the actuating supports 120 between the first position and second position (or any position therebetween, e.g., a third position) based on the clinician's needs and/or progression of the surgical procedure and in relation with the surgical instrument 20.

The clinician may monitor forces acting on the actuating supports 120 and adjust the position of the actuating supports 120 (e.g. heights thereof) to maintain a location or adjust a location of a patient (or body part thereof), as needed or desired. The ability for constant readjustment of the patient's position allows improved access to the patient throughout the entire medical procedure. Further, it enhances the robotic surgical system 1 performance and allows the patient to become an integral component of the medical procedure.

Upon completion of the medical procedure, the clinician may elect to keep the actuating supports 120 actuated and/or may elect to return the actuating supports 120 to the first position.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that varies other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modification and variations are also included within the scope of the present disclosure. Accordingly, the subject matter of the present disclosure is not limited by what has been particularly shown and described.

What is claimed is:

1. A method of positioning a patient during a medical procedure comprising:
    determining a desired initial position of the patient upon an actuating operating table system based upon parameters of the patient;
    positioning the patient upon the actuating operating table system;
    actuating an actuating system of the actuating operating table system to position the patient in the initial position;
    monitoring the initial position of the patient in relation to a surgical instrument; and
    actuating the actuating system to maintain the initial position of the patient in relation to the surgical instrument.

2. The method of positioning a patient during a medical procedure of claim 1, wherein actuating the actuating system of the operating table includes actuating at least one actuating support of the actuating system.

3. The method of positioning a patient during a medical procedure of claim 2, further comprising transitioning the at least one actuating support of the actuating system between a first position and a second position.

4. The method of positioning a patient during a medical procedure of claim 1, further comprising simultaneously moving the surgical instrument relative to the patient and actuating the actuating system.

5. The method of positioning a patient during a medical procedure of claim 1, further comprising monitoring the actuating system.

6. A method of positioning a patient during a medical procedure comprising:
    determining a desired initial position of the patient upon an actuating operating table system based upon parameters of the patient, the actuating operating table system including:
        at least one actuating section; and
        a plurality of actuating supports, wherein each of the plurality of supports includes a shaft assembly;
        wherein each of the plurality of actuating supports is configured to be activated individually, the shaft assembly of each of the plurality of actuating supports is configured to translate between a first position and a second position, wherein when an activated actuating support of the plurality of actuating supports is in the first position, the shaft assembly of the activated actuating support is aligned with the remaining of the plurality of actuating supports, and when an activated actuating support of the plurality of actuating supports is in the second position, the shaft assembly of the activated actuating support is misaligned with the remaining of the plurality of actuating supports;
    positioning the patient upon the actuating operating table system;
    actuating a select number of the plurality of actuating supports to position the patient in the initial position;
    monitoring the initial position of the patient in relation to a surgical instrument; and
    actuating the plurality of actuating supports of the actuating system to maintain the initial position of the patient in relation to the surgical instrument.

7. The method of positioning a patient during a medical procedure of claim 6, further comprising:
    actuating a select number of the plurality of actuating supports to maintain the initial position of the patient in relation to the surgical instrument.

8. The method of positioning a patient during a medical procedure of claim 6, wherein actuating the actuating operating table system includes actuating at least one actuating support of the actuating system.

9. The method of positioning a patient during a medical procedure of claim 8, further comprising transitioning the at least one actuating support of the actuating operating table system between a first position and a second position.

10. The method of positioning a patient during a medical procedure of claim 6, further comprising simultaneously moving the surgical instrument, and moving the patient by actuating the plurality of actuating supports of the actuating operating table system.

11. The method of positioning a patient during a medical procedure of claim 6, further comprising monitoring the actuating operating table system.

12. A method of positioning a patient during a medical procedure comprising:
    positioning the patient upon an actuating operating table system;
    actuating an actuating system of the actuating operating table system to position the patient in an initial position;
    monitoring the initial position of the patient in relation to a surgical instrument; and
    actuating the actuating system to maintain the initial position of the patient in relation to the surgical instrument.

13. The method of positioning a patient during a medical procedure of claim 12, wherein actuating the actuating system of the operating table includes actuating at least one actuating support of the actuating system.

14. The method of positioning a patient during a medical procedure of claim 12, further comprising transitioning the at least one actuating support of the actuating system between a first position and a second position.

15. The method of positioning a patient during a medical procedure of claim 12, further comprising simultaneously moving the surgical instrument, and moving the patient by actuating the plurality of actuating supports of the actuating system.

16. The method of positioning a patient during a medical procedure of claim 12, further comprising monitoring the actuating system.

\* \* \* \* \*